US007096056B2

(12) United States Patent
Miller et al.

(10) Patent No.: US 7,096,056 B2
(45) Date of Patent: Aug. 22, 2006

(54) FUNCTIONAL MAGNETIC RESONANCE IMAGING USING STEADY STATE FREE PRECESSION

(75) Inventors: Karla L. Miller, San Francisco, CA (US); John M. Pauly, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 342 days.

(21) Appl. No.: 10/463,008

(22) Filed: Jun. 16, 2003

(65) Prior Publication Data

US 2004/0254446 A1 Dec. 16, 2004

(51) Int. Cl.
*A61B 5/05* (2006.01)
*G01V 3/00* (2006.01)

(52) U.S. Cl. .................. 600/410; 600/407; 600/408; 600/423; 324/306; 324/309; 324/318; 324/322

(58) Field of Classification Search ..................... None
See application file for complete search history.

(56) References Cited

U.S. PATENT DOCUMENTS

| 6,271,665 B1 * | 8/2001 | Berr et al. | 324/306 |
| 6,307,368 B1 * | 10/2001 | Vasanawala et al. | 324/309 |
| 6,400,978 B1 * | 6/2002 | Teicher et al. | 600/410 |
| 2004/0092809 A1 * | 5/2004 | DeCharms | 600/410 |

OTHER PUBLICATIONS

Scheffler and Hennig, "Is TrueFISP a Gradient-Echo or a Spin-Echo Sequence?" Magnetic Resonance in Medicine 49:395-397 (2003).

Scheffler et al., "Detection of BOLD changes by means of a frequency-sensitive true FISP technique: preliminary results," NMR in Biomedicine 14:490-496 (2001).

Ogawa et al., "Brain magnetic resonance imaging with contrast dependent on blood oxygenation," Proc. Natl. Acad. Sci., USA, vol. 87, pp. 9868-9872, Dec. 1990.

Ogawa et al., "Instrinsic signal changes accompanying sensory stimulation: Functional brain mapping with magnetic resonance imaging," Proc. Natl. Acad. Sci., USA, vol. 89, pp. 5951-5955, Jul. 1992.

Kwong et al., "Dynamic magnetic resonance imaging of human brain activity during primary sensory stimulation," Proc. Natl. Acad. Sci., USA, vol. 89, pp. 5675-5679, Jun. 1992.

* cited by examiner

*Primary Examiner*—Brian L. Casler
*Assistant Examiner*—John F. Ramirez
(74) *Attorney, Agent, or Firm*—Beyer Weaver & Thomas LLP

(57) ABSTRACT

A method for functional magnetic resonance imaging (fMRI) uses steady-state free precession (SSFP) to image changes in blood oxygenation between two time periods. A center frequency of the SSFP sequence is placed between the different resonant frequencies for oxyhemoglobin and deoxyhemoglobin whereby the signals have a phase difference of 180° and tend to cancel. By repeating the SSFP imaging sequence at different times, the difference in the measured signals provides a measure of change in oxyhemoglobin. RF flip angle of the SSFP sequence is chosen to maximize signal level in the frequency range from that of water in the presence of oxyhemoglobin and that of water in the presence of deoxyhemoglobin.

14 Claims, 6 Drawing Sheets

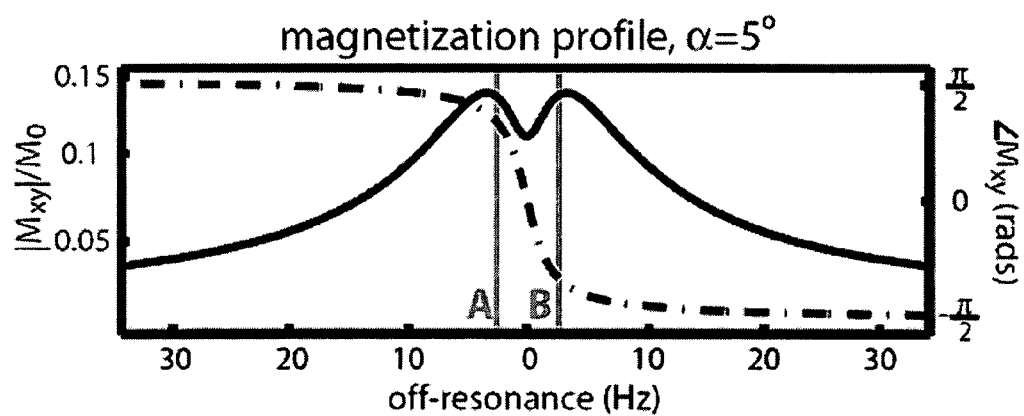
FIG. 3
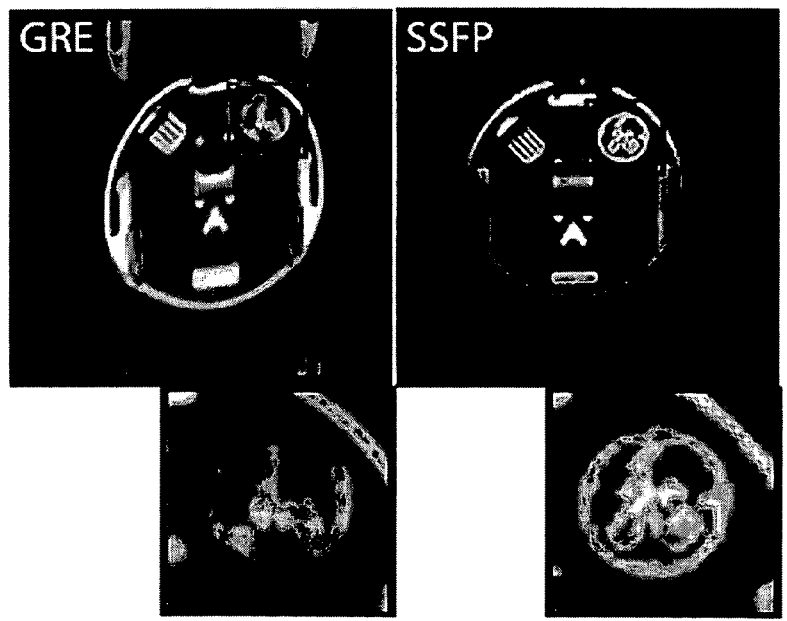
FIG. 4B  FIG. 4A

FUNCTIONAL MAGNETIC RESONANCE IMAGING USING STEADY STATE FREE PRECESSION

GOVERNMENT RIGHTS

The U.S. government has rights in the disclosed invention pursuant to NIH grants to Stanford University including NIH-1P41 RR09784.

BACKGROUND OF THE INVENTION

This invention relates generally to magnetic resonance imaging (MRI), and more particularly the invention relates to functional MRI using steady state free precession (SSFP).

Magnetic resonance imaging (MRI) provides excellent soft tissue contrast with arbitrary scan-volume orientations, thus making MRI an extremely useful medical imaging modality. However, in many applications, MRI is limited by long scan times, limited spatial resolution, and magnetic field homogeneity. Recent advances in gradient amplifier technology have enabled the use of fully-refocused steady-state free precession (SSFP) imaging methods. SSFP imaging is a very fast method that can provide high SNR efficiency and high resolution. A number of commercial implementations of SSFP are available, all of which conceptually identical.

Functional Magnetic Resonance Imaging (fMRI) has revolutionalized neuroscience by mapping activity throughout the brain without the use of radioactive tracers, electrical probes or other invasive procedures. The dominant method for fMRI, Blood Oxygenation Level Dependent (BOLD) imaging is sensitive to changes in blood oxygenation that occur in response to brain activity. See, for example, Ogawa et al., "Intrinsic Signal Changes Accompanying Sensory Stimulation: Functional Brain Mapping With Magnetic Resonance Imaging," Proc Natl Acad Sci, USA, 89:5951–5955, 1992. The BOLD method is based on the sensitivity of the MR signal to deoxyhemoglobin, which has a resonance frequency that is shifted relative to water. BOLD fMRI uses Gradient Recalled Echo (GRE) imaging with a long echo time (TE) to increase the signal dephasing due to the deoxyhemoglobin frequency shift, resulting in signal levels that depend on the concentration of deoxyhemoglobin in the blood. While BOLD imaging represents a major advance in brain mapping, this method has a number of important limitations including poor spatial resolution, low signal levels, limited contrast and severe image artifacts. These limitations derive from the fact that BOLD contrast is coupled to sources of image degradation and signal loss.

SUMMARY OF THE INVENTION

In accordance with the invention, steady state free precession is used in implementing functional magnetic resonance imaging. SSFP is intrinsically sensitive to resonance frequency of an imaged material. The signal phase in SSFP is approximately a square-wave function of resonant frequency. Near resonance, the phase changes rapidly by $\pi$ radians. Off-resonance, the phase is flat.

Since oxygenated and deoxygenated blood have different resonance frequencies, setting the center frequency in a SSFP sequence between the oxyhemoglobin and deoxyhemoglobin resonance frequencies places them on opposite sides of the phase change. Alternatively, the angle used for RF phase cycling can be used to separate the phases of oxyhemoglobin and deoxyhemoglobin. Thus, signal from water and oxygenated blood will have the opposite sign of deoxygenated blood. Within a voxel consisting primarily of spins near the water/oxyhemoglobin frequency, the signal from deoxyhemoglobin will subtract from the larger water and oxyhemoglobin signal. During increased metabolic activity, a portion of the deoxygenated pool becomes oxygenated, resulting in an increase in the voxel signal. Since the signal change is due to a pool of spins that change from deoxygenated (negative signal) to oxygenated (positive signal), the signal change is roughly twice the size of the exchanging pool. Similar dynamics will cause a signal decrease if the oxyhemoglobin concentration increases in a voxel that has its primary resonance frequency at the deoxyhemoglobin shift.

The invention and object and features thereof will be more readily apparent from the following detailed description and appended claims when taken with the drawings.

BRIEF DESCRIPTION OF THE DRAWINGS

FIG. 3 illustrates SSFP signal magnitude (solid) and phase (dashed) as a function of resonance frequency as employed in the present invention.

FIGS. 4A, 4B are images reconstructed with the present invention and with prior art BOLD imaging, respectively.

DETAILED DESCRIPTION OF ILLUSTRATED EMBODIMENTS

Figure 1A:
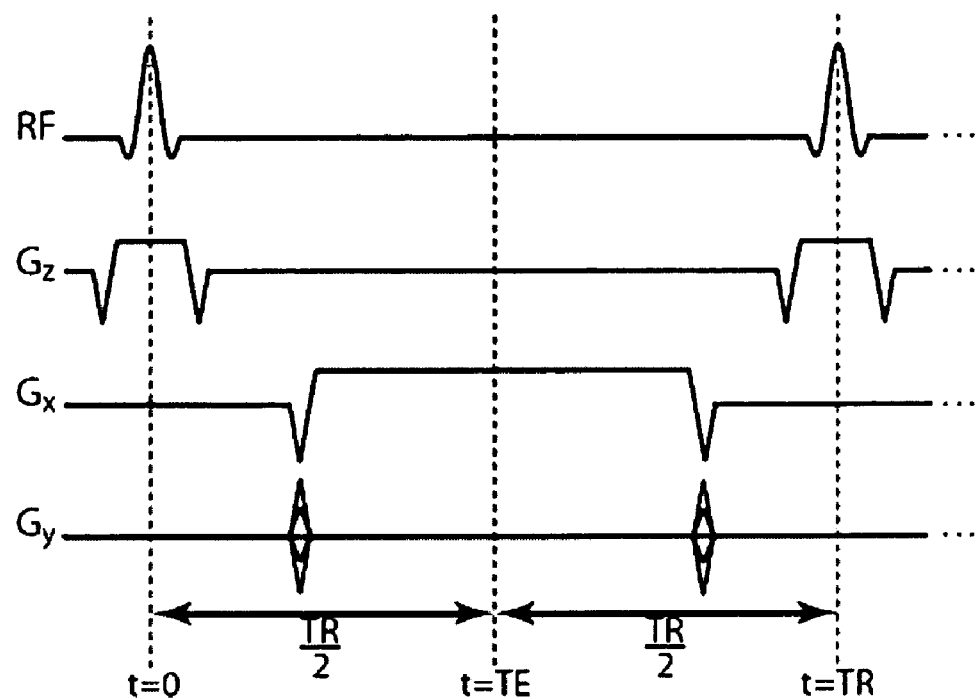
FIGS. 1A, 1B illustrate a SSFP phase sequence in accordance with prior art.
Figure 1B:
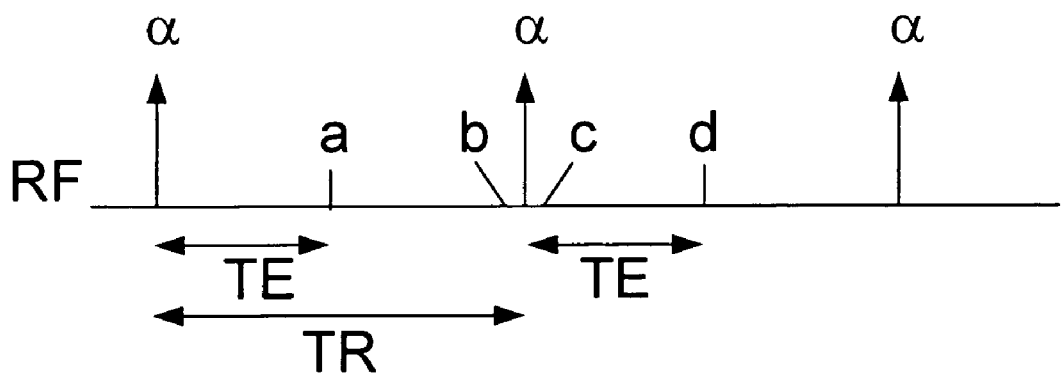

As illustrated in FIGS. 1A, 1B, a refocused SSFP sequence includes a single RF excitation which is repeated periodically. All gradients used for slice selection or imaging are fully rewound over each repetitive time, TR. In the steady-state, the magnetization at points a and d is the same.

Magnetization is tipped about a traverse axis through an angle $\alpha$. Between excitations, the magnetization undergoes a precession by an angle $\theta = 2\pi \Delta f TR$ about the z-axis, where $\Delta f$ is the tissue off-resonance, and also experiences both T1 and T2 relaxation.

During the sequence each spin is affected by RF pulses, relaxation and free precession. The steady-state magnetization for SSFP is a function of the sequence parameters flip angle ($\alpha$), repetition time (TR) and echo time (TE) as well as the tissue parameters T1, T2, and resonant frequency shift $\Delta f$.

Figure 2A:
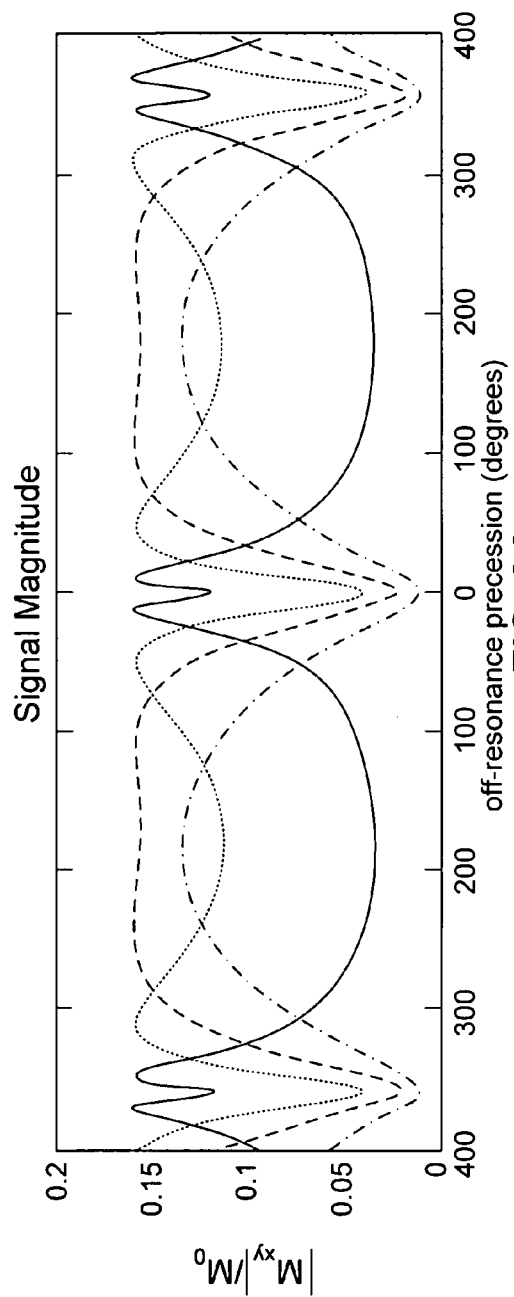
FIGS. 2A, 2B, 2C and 2D illustrate SSFP signal magnitude and phase, respectively, for different flip angles.

All imaging gradients are rewound, and the low spatial frequency-information is acquired at an echo time (TE) midway between RF excitation pulses. The steady-state signal that arises after many repetitions is shown in FIG. 2A. The signal magnitude is a strong function of the resonant frequency, exhibiting a characteristic pattern that repeats every 1/TR Hz. The magnitude varies for different flip angles and relaxation times T1 and T2 as is typical for MRI sequences.

Figure 2B:
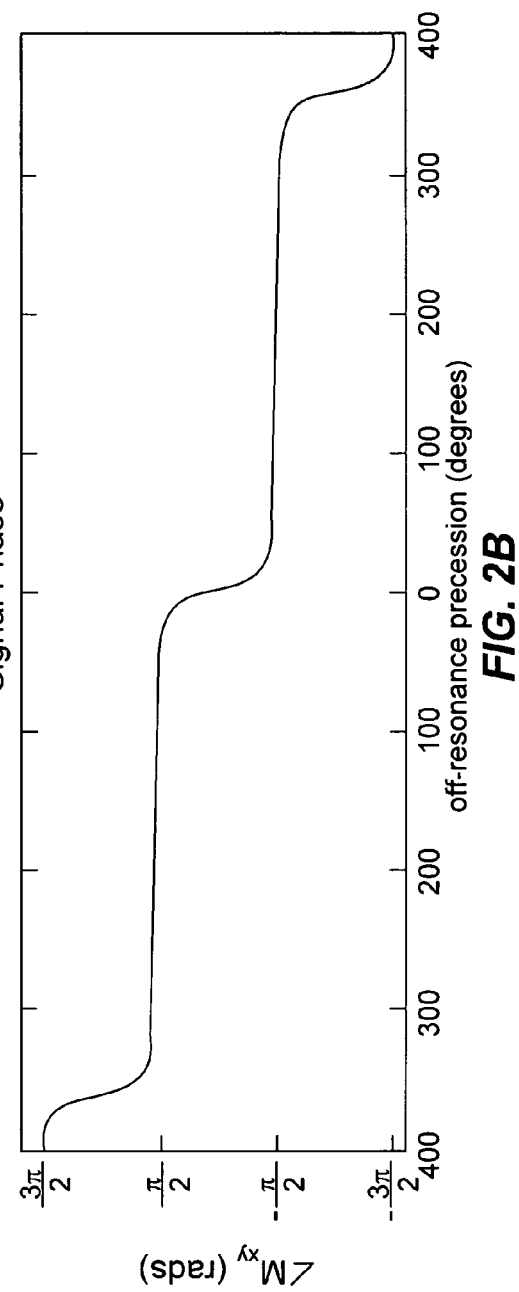

FIGS. 2A and 2B illustrate SSFP signal magnitude and phase, respectively, as a function of flip angles. Three different flip angles are shown including $\alpha=5°$ (solid line), $\alpha=15°$ (dotted line), $\alpha=30°$ (dashed line) and $\alpha=60°$ (dash and dot line), and their effect on signal magnitude.

The signal phase in SSFP is, to a good approximation, a square-wave function of resonant frequency. Near resonance, the phase changes rapidly by $\pi$ radians. Off-resonance, the phase is very flat.

The present invention uses steady state free precession (SSFP) imaging, which is intrinsically sensitive to resonance frequency, to sense the deoxyhemoglobin shift more directly. With proper placement of the center frequency, SSFP images are made sensitive to blood oxygenation, yielding an fMRI method that gathers data under significantly better imaging conditions than GRE BOLD imaging. Steady-state fMRI thus obtains high-SNR, unartifacted images with high spatial resolution. Steady-state fMRI, in accordance with the invention, inverts the deoxyhemoglobin signal relative to the water and oxyhemoglobin signal, resulting in a signal change that is approximately twice the size of the change in blood oxygenation. This results in a much larger percent signal change than is created in BOLD imaging. A previous proposal for steady-state fMRI by Scheffler and colleagues, "Detection of BOLD Changes by Means of a Frequency-Sensitive trueFISP Technique: Preliminary Results," NMR Biomed, 14:490–496, 2001, utilized the signal null found at higher flip angles. This method places either the oxyhemoglobin or deoxyhemoglobin resonance frequency in the signal null and thus has smaller signal change than the method proposed here.

Figure 2C:
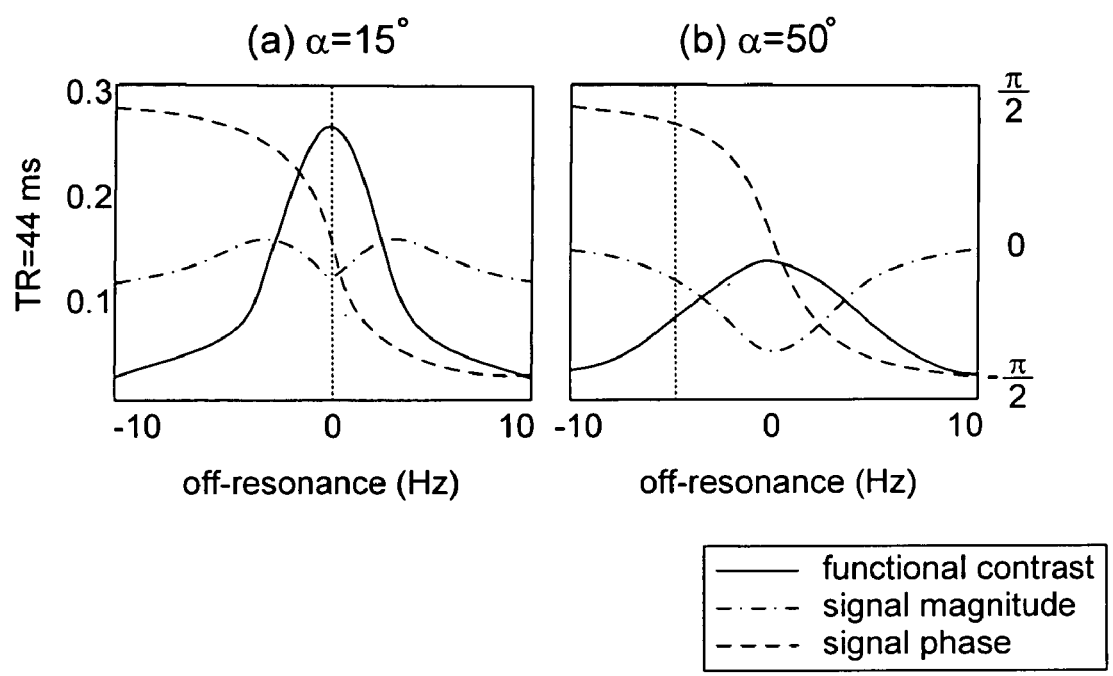
Figure 2D:
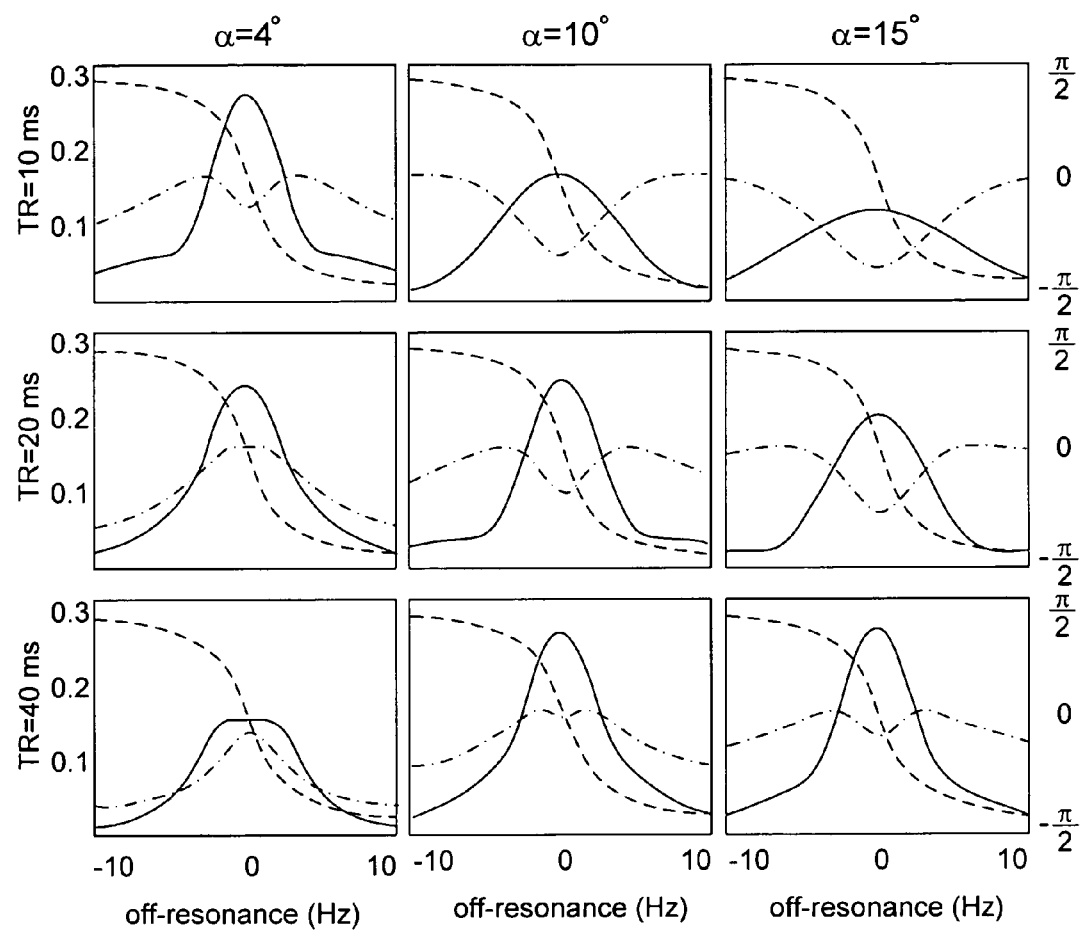

The present invention uses a low flip angle to achieve high signal near the phase transition, resulting in strong functional contrast that is approximately twice the size of the change in blood oxygenation. For a particular TR, this method can be optimized based on the flip angle. To achieve maximum functional contrast, the flip angle with greatest contrast can be chosen. For example, Scheffler and colleagues used TR=44 ms, $\alpha$=50° and set the resonance frequency equal to the deoxyhemoglobin frequency. For this TR, the functional contrast is approximately 3 times greater with $\alpha$=15° and placement of the center frequency between the oxyhemoglobin and deoxyhemoglobin frequencies as in the present invention. See FIG. 2C for example. Alternatively, to reduce sensitivity to drift in the resonance frequency, the flip angle can be chosen to achieve uniformity of contrast over a range of resonance frequencies. For TR=40 ms, reducing the flip angle from 15° to 4° halves the functional contrast but also results in more uniform contrast near resonance. This is illustrated in FIG. 2D for flip angles, $\alpha$, of 4°, 10°, and 15° and TR equal to 10 ms, 20 ms, and 40 ms.

As above described, SSFP uses a rapidly-repeating series of RF pulses and imaging gradients (FIG. 1) to establish signal that is highly sensitive to resonance frequency (FIG. 3). This signal profile is a periodic function of resonance frequency, repeating every 1/TR Hz. The phase of the magnetization undergoes an abrupt phase change of 180° over a narrow band of frequencies near resonance (dashed line in FIG. 3). Outside of this transition band, the phase is essentially flat, with positive and negative frequencies separated by 180°. This phase change can also be thought of as a change of sign in the signal. At low flip angles, this phase transition coincides with the peak of the signal magnitude.

Since oxygenated and deoxygenated blood have different resonance frequencies, setting the center frequency between the oxyhemoglobin and deoxyhemoglobin resonance frequencies places them on opposite sides of the phase change (A and B in FIG. 3). In this arrangement, signal from water and oxygenated blood will have the opposite sign of deoxygenated spins. Within a voxel, the signal from deoxyhemoglobin will subtract from the larger water and oxyhemoglobin signal. During activation, a portion of the deoxygenated pool becomes oxygenated, resulting in an increase in the voxel signal. Since the signal change is due to a pool of spins that change from deoxygenated (negative signal) to oxygenated (positive signal), the signal change is roughly twice the size of the exchanging pool.

A major advantage to imaging with SSFP is the drastically improved image quality and SNR. Steady-state imaging has extraordinarily high SNR efficiency because an unusually large fraction of the total imaging time is spent collecting data. In contrast, the long-TE GRE sequences used in BOLD fMRI have unusually low SNR since a major portion of the signal must decay in order for BOLD contrast to develop. Additionally, BOLD images tend to have major warping artifacts and signal dropout due to the heavy $T^*_2$ contrast. When imaging with an echo time of TE=TR/2, SSFP has no $T^*_2$ effects, and therefore experiences no image warping or signal dephasing. FIG. 4 compares the image quality for phantom images acquired using typical scan parameters for fMRI using EPI-GRE and 2DFT-SSFP at the same resolution and frame rate. The EPI-GRE images exhibit significant warping and ghosting, while the 2DFT-SSFP images have no such artifacts. In addition, the GRE images do not appear to have the same effective resolution as the SSFP images (see insets of FIG. 4) despite the fact that both acquisitions cover the same extent in k-space.

A functional SSFP method in accordance with the invention was tested at 1.5T with a simple visual paradigm (in which the subject viewed a 10 Hz reversing annulus grating in 15 s on/15 s off blocks for 2 minutes). A sagittal slice through the occipital pole (24 cm FOV, 128×64, 2DFT trajectory) was gathered every 0.5 seconds with the center of k-space gathered halfway through the TR (TR/TE=7.8/3.9 ms). Linear shimming was targeted to the occipital pole. This data was analyzed with standard fMRI techniques using Brain Voyager (1.5 s temporal and 1.8×3.75 mm² spatial filtering). The results for this experiment are shown in FIG. 4. Stimulus-correlated signal changes of 4–5% were found exclusively in the occipital lobe.

Figure 5:
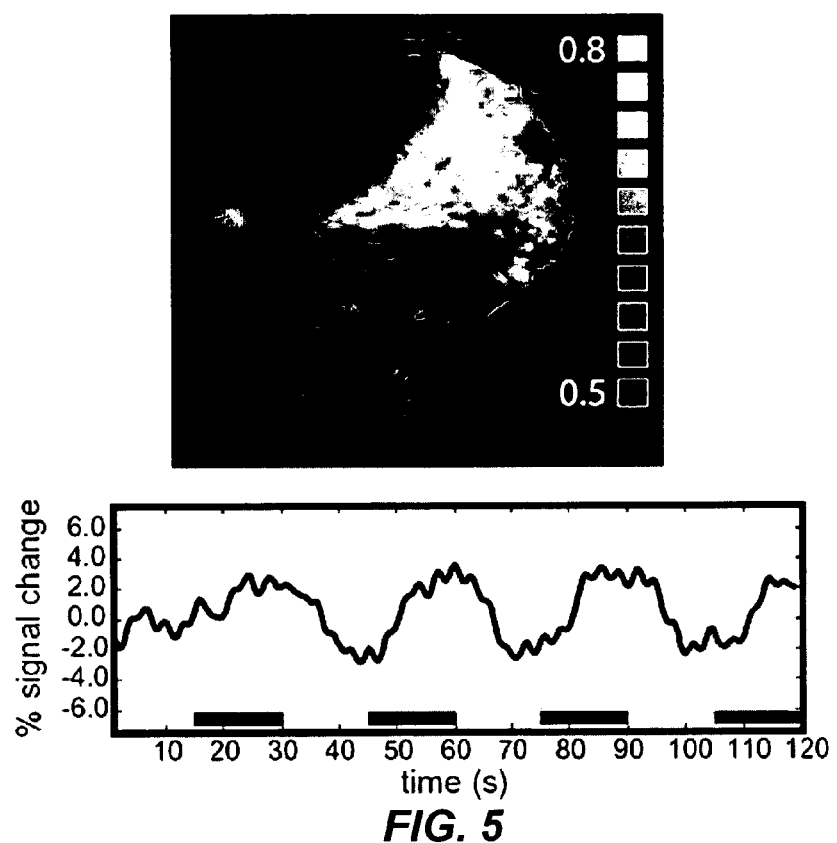
FIG. 5 illustrates an activation mask and a ROI-averaged time-course for a single frequency experiment.
Figure 6:
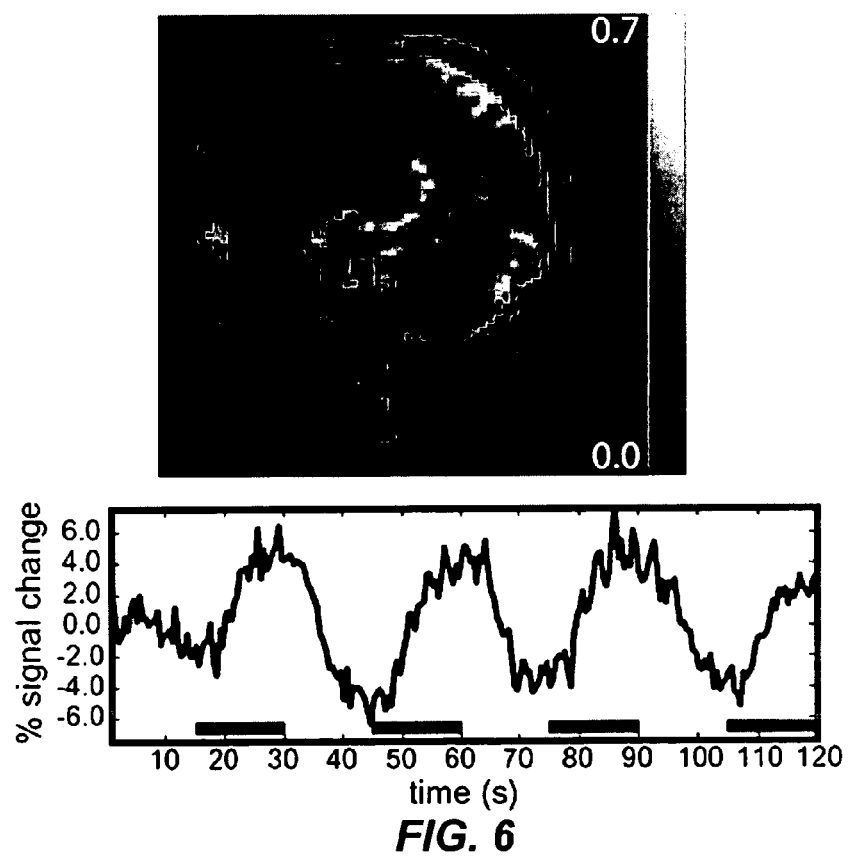
FIG. 6 illustrates an activation mask and a ROI-averaged time-course for a multi-frequency experiment.

It was noted that the magnetic field varied across the occipital pole such that not all regions had the same resonance frequency. To address this, the experiment was repeated at 4 frequency offsets ($\Delta f$=0,4,8,12 Hz). This data was processed using a custom analysis that selected the frequency with maximum stimulus correlation for each voxel. This multi-frequency analysis identified a similar region but contained larger signal changes (7–8%) (FIG. 6). Both FIGS. 5 and 6 display the activation masks on the actual SSFP images gathered during the experiment.

Another advantage of functional SSFP is the high contrast of the functional signal. In functional SSFP, the pool of spins that change from deoxygenated to oxygenated during activation are completely inverted in activation as compared to the resting state. In BOLD imaging, this signal component is simply attenuated. For this reason, functional SSFP is expected to have significantly better functional contrast than BOLD imaging. Early support for this effect can be seen by noting that the signal changes found in FIG. 6 are several times larger than typical BOLD signals at 1.5T.

The phase profile shown in FIG. 2b applies to a standard SSFP imaging sequence where the echo time is midway between RF excitation pulses. A number of trajectories can acquire an echo in this manner, including Cartesian (or, 2DFT) imaging, radial SSFP imaging, echo-planar imaging, or spiral in-out imaging. However, the mechanism for functional contrast using SSFP imaging described herein does not require this echo time. The use of an echo time other than TR/2 changes the phase profile outside of the transition region but has little effect on the transition itself. Since the transition is the source of functional contrast, this implies that functional contrast is largely independent of echo time.

In summary, the invention provides a new functional imaging technique that uses standard SSFP imaging with careful placement of the center frequency relative to blood and water resonance frequencies. The invention exploits the frequency sensitivity of SSFP to create a signal that depends on the blood oxygenation and can be used to measure hemodynamic changes.

While the invention has been described with reference to specific embodiments, the description is illustrative of the invention and is not to be construed as limiting the invention. Various modifications and applications may occur to those skilled in the art without departing from the true scope and spirit of the invention as defined by the appended claims.

What is claimed is:

1. A method for functional magnetic resonance imaging (fMRI) comprising the steps of:
    a) applying a steady-state free precession (SSFP) imaging sequence to a body having oxyhemoglobin and deoxyhemoglobin therein, with the oxyhemoglobin and the deoxyhemoglobin having different resonance frequencies, a center frequency of the SSFP sequence being between the resonance frequencies, and
    b) measuring MRI signals from the body whereby signals from water in the presence of deoxyhemoglobin subtract from signals from water in the presence of oxyhemoglobin thereby providing a measure of difference in oxyhemoglobin and deoxyhemoglobin.

2. The method as defined by claim 1 wherein step a) and step b) are repeated at different times and a difference in the measured signals from step b) at the different times provides a measure of change in blood oxygenation.

3. The method as defined by claim 2 wherein the signal change is approximately twice the change between deoxyhemoglobin and oxyhemoglobin.

4. The method as defined by claim 3 wherein the center frequency is midway between the resonance frequencies of water in the presence of oxyhemoglobin and water in the presence of deoxyhemoglobin.

5. The method as defined by claim 4 wherein the phases of the MRI signals for oxyhemoglobin and for deoxyhemoglobin differ by approximately $\pi$ radians.

6. The method as defined in claim 3, wherein the SSFP imaging sequence includes a RF flip angle chosen to maximize the magnitude of the signal change.

7. The method as defined by claim 1 wherein the center frequency is midway between the resonance frequencies of water in the presence of oxyhemoglobin and water in the presence of deoxyhemoglobin.

8. The method as defined by claim 6 wherein the phases of the MRI signals for oxyhemoglobin and for deoxyhemoglobin at the center frequency differ by approximately $\pi$ radians.

9. The method as defined in claim 1, wherein the SSFP imaging sequence includes a RF flip chosen to maximize the signal level in the frequency range from that of water in the presence of oxyhemoglobin and that of water in the presence of deoxyhemoglobin.

10. A method of measuring change in blood oxygenation in a body using magnetic resonance imaging comprising the steps of:
    a) placing the body in a magnetic field,
    b) applying axial magnetic fields to the body,
    c) applying a plurality of RF excitation pulses to the body at a repetition time, TR, to flip nuclei spins,
    d) rewinding all gradients over the repetition time, TR,
    e) measuring refocused MRI signals at time TE whereby the phases of the measured signals for oxyhemoglobin and deoxyhemoglobin differ by approximately 180°,
    f) repeating steps a) through e) at a second time period differing from a first time period for steps a)–e), and
    g) using the measured refocused MRI signals from step e) and repeated step e) to measure change in blood oxygenation from the first time period to the second time period.

11. The method as defined by claim 10 wherein step h) subtracts the measured refocused MRI signals, whereby signal change is a measure of change between deoxyhemoglobin and oxyhemoglobin.

12. The method as defined by claim 11 wherein the signal change is indicative of twice the change between deoxyhemoglobin and oxyhemoglobin.

13. The method as defined by claim 12 wherein the center frequency is midway between the resonance frequencies.

14. The method as defined by claim 10 wherein the center frequency is midway between the resonance frequencies.

* * * * *